United States Patent
Matsushima et al.

(10) Patent No.: US 8,552,204 B2
(45) Date of Patent: Oct. 8, 2013

(54) ZINC CLUSTER

(75) Inventors: Yoshimasa Matsushima, Hiratsuka (JP); Hideki Nara, Hiratsuka (JP); Takahiro Fujiwara, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 32 days.

(21) Appl. No.: 13/395,312

(22) PCT Filed: May 31, 2010

(86) PCT No.: PCT/JP2010/059204
§ 371 (c)(1),
(2), (4) Date: Mar. 9, 2012

(87) PCT Pub. No.: WO2011/030591
PCT Pub. Date: Mar. 17, 2011

(65) Prior Publication Data
US 2012/0172601 A1    Jul. 5, 2012

(30) Foreign Application Priority Data
Sep. 11, 2009   (JP) ................................. 2009-210208

(51) Int. Cl.
| | | |
|---|---|---|
| *C07D 263/12* | (2006.01) | |
| *C07D 309/12* | (2006.01) | |
| *C07F 3/06* | (2006.01) | |
| *C07C 229/08* | (2006.01) | |
| *C07C 67/03* | (2006.01) | |

(52) U.S. Cl.
USPC ............. 548/239; 560/41; 560/105; 560/106; 549/420; 556/130

(58) Field of Classification Search
None
See application file for complete search history.

(56) References Cited

U.S. PATENT DOCUMENTS

2009/0198070 A1    8/2009   Mashima et al.

FOREIGN PATENT DOCUMENTS

| HU | 207 089 B | 3/1993 |
|---|---|---|
| WO | WO 2007/066617 A1 | 6/2007 |
| WO | WO 2009/047905 A1 | 4/2009 |

OTHER PUBLICATIONS

"Jikken Kagaku Kouza (Experimental Chemistry Course), Muki Sakutai Kireto Sakutai (Inorganic Complexes and Chelate Complexes)," 1991, Maruzen Publishing Co., Ltd., Fourth Edition, pp. 451-452, vol. 17.

Nockemann, Peter, et al., "Polynuclear Metal Complexes Obtained from the Task-Specific Ionic Liquid Betainium Bistriflimide," Crystal Growth & Design, 2008, pp. 1353-1363, vol. 8, No. 4.

Ohshima, Takashi, et al., "Direct conversion of esters, lactones, and carboxylic acids to oxazolines catalyzed by a tetranuclear zinc cluster," Chem. Commun., 2006, pp. 2711-2713.

*Primary Examiner* — Alicia L Otton
(74) *Attorney, Agent, or Firm* — Sughrue Mion, PLLC (57) ABSTRACT

Disclosed is a novel zinc cluster compound represented by general formula (1): $Zn_4O(OCOR)_6(RCOOH)_n$, wherein R represents an alkyl group which has 1 to 4 carbon atoms and may be substituted with a halogen atom, and n represents 0.1 to 1, and also disclosed are a method for producing the compound and a reaction using the compound.

4 Claims, 5 Drawing Sheets

ZINC CLUSTER

CROSS REFERENCE TO RELATED APPLICATION

This application is a National Stage of International Application No. PCT/JP2010/059204, filed on May 31, 2010, claiming priority based on Japanese Patent Application No. 2009-210208, filed Sep. 11, 2009, the contents of all of which are incorporated herein by reference in their entirety.

TECHNICAL FIELD

The present invention relates to a zinc cluster useful as an organometallic catalyst and catalytic reactions using the zinc cluster such as transesterification reaction, esterification reaction, reaction for direct formation of oxazolines from carbonyl compounds, and amidation reaction.

BACKGROUND ART

A zinc tetranuclear cluster $Zn_4O\ (OCOR)_6$ containing zinc atoms as a nuclear metal is known to be produced by subjecting a zinc carboxylate salt such as zinc (II) acetate hydrate to high-temperature (250° C. or above) heating conditions under vacuum (Non Patent Document 1).

Moreover, when zinc trifluoroacetate hydrate is used, a zinc tetranuclear cluster $Zn_4O\ (OCOCF_3)_6$ can be obtained under the above-described reaction conditions. Furthermore, the zinc tetranuclear cluster $Zn_4O\ (OCOCF_3)_6$ is known to be useful as a catalyst for esterification reaction, transesterification reaction, acylation reaction, and amidation reaction (Patent Document 1).

In other words, the use of the zinc tetranuclear cluster $Zn_4O\ (OCOR)_6$ as a catalyst allows the reactions to proceed efficiently under mild conditions. In addition, the zinc tetranuclear cluster catalyst having zinc atoms with a relatively low toxicity as a nuclear metal is known to be useful because of its environmentally benign characteristics (Non Patent Document 2).

Citation List
Patent Literature
Patent Literature 1: WO2007/066617
Non Patent Literatures
Non Patent Literature 1: Jikken Kagaku Kouza (Experimental Chemistry Course), fourth edition, (1991), vol. 17, (Muki Sakutai·Kireto Sakutai (Inorganic Complexes and Chelate Complexes)), p. 451 to 452, (published by Maruzen Publishing Co., Ltd.)
Non Patent Literature 2: Chem. Commun. 2006, p. 2711.

SUMMARY OF INVENTION

An object of the present invention is to supply a zinc cluster having catalytic performances equivalent to those of a conventionally known zinc tetranuclear cluster $Zn_4O\ (OCOR)_6$ in larger quantities at lower costs under milder conditions.

The present invention enables the production using a zinc carboxylate compound such as zinc acetate hydrate or zinc trifluoroacetate hydrate as a raw material under temperature conditions milder than those in conventional cases. In addition, it has been found that the zinc cluster of the present invention exhibits catalytic activities equivalent to those of a conventional zinc cluster $Zn_4O\ (OCOR)_6$ in transesterification reaction, esterification reaction, reaction for direct formation of oxazolines from carbonyl compounds, and amidation reaction.

The present invention relates to the following items [1] to [4].
[1] A zinc cluster represented by general formula (1):

$$Zn_4O\ (OCOR)_6\ (RCOOH)_n \quad (1),$$

wherein R represents an alkyl group having 1 to 4 carbon atoms which optionally has one or more halogen atoms, and n represents 0.1 to 1.
[2] A method for producing the zinc cluster according to the above-described item [1], comprising
performing a reaction by heating a zinc carboxylate hydrate represented by general formula (2):

$$Zn\ (OCOR)_2 \cdot xH_2O \quad (2),$$

wherein R represents an alkyl group having 1 to 4 carbon atoms which optionally has one or more halogen atoms, and x represents any number not less than 0 at a temperature of 50° C. to 200° C.
[3] A method for acylating a hydroxyl group with a carboxylic acid or an ester thereof, comprising
using the zinc cluster according to the above-described item [1] as a catalyst.
[4] A method for producing an oxazoline by a reaction of a carboxylic acid or an ester thereof with an amino alcohol, comprising
using the zinc cluster according to the above-described item [1] as a catalyst.

The zinc cluster represented by the general formula (1) of the present invention exhibits excellent catalytic activities, and makes it possible to perform reactions under mild reaction conditions with excellent environmental friendliness, operability, and economy. The zinc cluster of the present invention is also useful as a catalyst for synthesis of intermediates for pharmaceuticals and agricultural chemicals and further as a precursor compound for zinc oxide.

DESCRIPTION OF EMBODIMENTS

Hereinafter, the present invention will be described specifically.

A zinc cluster of the present invention is represented by the following general formula (1):

$$Zn_4O\ (OCOR)_6\ (RCOOH)_n \quad (1)$$

In the formula (1), R represents an alkyl group having 1 to 4 carbon atoms which optionally has one or more halogen atoms, and n represents a value in a range from 0.1 to 1. Examples of non-substituted alkyl groups serving as the alkyl group include a methyl group, an ethyl group, a propyl group, an isopropyl group, a butyl group, an isobutyl group, a s-butyl group, and a t-butyl group. Meanwhile, examples of the halogen atoms include fluorine, chlorine, bromine, and iodine atoms. Examples of the alkyl group having one or more halogen atoms include perfluoroalkyl groups such as a trichloromethyl group, a tribromomethyl group, a trifluoromethyl group, a pentafluoroethyl group, a heptafluoropropyl group, and a heptafluoroisopropyl group; and the like. Of these groups, a preferred group is a trifluoromethyl ($CF_3$) group.

Meanwhile, it is desirable that the numeric value of n is preferably in a range from 0.1 to 0.9, and further preferably in the range from 0.5 to 0.9. The zinc cluster of the present invention contains the zinc cluster represented by $Zn_4O$ $(OCOR)_6$ (RCOOH) as a main component, but may be a mixture with $Zn_4O$ $(OCOR)_6$ which is a conventionally known zinc cluster. In such a case, the zinc cluster of the present invention can be represented by $Zn_4O$ $(OCOR)_6$ $(RCOOH)_n$.

When R is a trifluoromethyl ($CF_3$) group, the content of zinc takes a value in a range from 24.7 wt % to 27.1 wt %. Further preferably, the content of zinc is desirably in a range from 24.7 wt % to 25.8 wt %.

The zinc cluster represented by the general formula (1) can be obtained by heating a zinc carboxylate hydrate represented by the following general formula (2):

$$Zn\ (OCOR)_2 . xH_2O \qquad (2)$$

(in the formula (2), R has the same meaning as described above, and x represents any numeric value not less than 0, and is generally in a range from 1 to 3).

Specifically, the zinc cluster of the present invention can be produced by heating the zinc carboxylate hydrate without any solvent or in a solvent, and efficiently discharging water and a carboxylic acid RCOOH, which are eliminated during the formation of the zinc cluster, to the outside of the system. The heating may be performed at an atmospheric pressure, and is preferably performed under vacuum. In addition, a heating temperature is desirably at or above a temperature at which water and the carboxylic acid RCOOH can be removed from the zinc carboxylate hydrate serving as the raw material. Specifically, the heating temperature is desirably 100° C. or above at an atmospheric pressure. Under vacuum, water and the carboxylic acid RCOOH can be removed at a temperature of 100° C. or below. The temperature may be any, as long as the temperature is not lower than a temperature at which water and the carboxylic acid RCOOH can be removed at the degree of vacuum. For example, in a case of 290±10 mmHg, the zinc cluster of the present invention can be formed at 75° C. or above.

The zinc cluster of the present invention can be produced under a temperature condition not higher than a temperature at which the raw material in a solid condition sublimates without being liquefied in a solvent-less condition. Meanwhile, when the production is performed in a solvent, any solvent can be used, as long as the solvent does not affect the formation of the zinc cluster of the present invention. Preferred solvents are low-polarity organic solvents. For example, benzene, toluene, xylene, hexane, heptane, octane and the like can be used. Aromatic solvents such as benzene, toluene, and xylene are further preferable. In other words, a preferred solvent is one which is capable of dissolving the zinc carboxylate hydrate ($Zn\ (OCOR)_2 . xH_2O$) at the production temperature, and in which the zinc cluster of the present invention has a low solubility. As described above, the zinc cluster of the present invention can be produced under a temperature condition lower than temperature conditions (250° C., 360° C.) for producing conventional zinc clusters. The zinc cluster of the present invention is produced preferably at 200° C. or below, and further preferably at 100° C. or below.

The zinc cluster represented by the general formula (1) of the present invention and obtained under the above-described condition sometimes may have high hygroscopicity or may be unstable in the air. Hence, it is preferable to treat the zinc cluster in the presence of an inert gas with a small water content. Preferred examples of the inert gas include nitrogen, argon, and the like.

The zinc cluster of the present invention can be used as a catalyst for, for example, (i) acylation reaction of a hydroxyl group (preferably an alcoholic hydroxyl group) with a carboxylic acid or an ester thereof, (ii) amidation reaction in which a carboxylic acid or an ester thereof is reacted with an amine, and (iii) a method for producing an oxazoline in which a carboxylic acid or an ester thereof is reacted with an amino alcohol, as described in WO2007/066617A1 or WO2009/047905A1.

The amount of the zinc cluster of the present invention used as a catalyst is not particularly limited, but zinc atoms are at a ratio of generally 0.001 to 0.9 mol, more preferably 0.001 to 0.3 mol, and further preferably 0.001 to 0.1 mol, relative to 1 mol of a raw material.

The reactions are generally performed in a solvent. The solvent is not particularly limited, and specific examples thereof include aromatic solvents such as toluene, xylene, and chlorobenzene; aliphatic hydrocarbon solvents such as hexane, heptane, and octane; ether solvents such as diethyl ether, diisopropyl ether, tert-butyl methyl ether, tetrahydrofuran, and 1,4-dioxane; amide solvents such as dimethylformamide (DMF), dimethylacetamide (DMAc), and N-methylpyrrolidone (NMP); dimethyl sulfoxide (DMSO), and the like. The reactions can be performed even in no solvent.

In addition, a reaction accelerator can also be added in the case of the acylation reaction of a hydroxyl group (preferably an alcoholic hydroxyl group) with a carboxylic acid or an ester thereof described in the item (i). Examples of the reaction accelerator include amines, and examples of the amines include primary amines such as ethylamine, n-propylamine, n-butylamine, and cyclohexylamine; secondary amines such as diethylamine, dipropylamine, diisopropylamine, and dicyclohexylamine; and tertiary amines such as triethylamine, diisopropylethylamine, tributylamine, and pyridine; and the like.

The various reactions using the zinc cluster of the present invention can be performed in the air, or under an inert gas such as nitrogen gas or argon gas. A reaction time is not particularly limited, and is generally approximately 1 to 45 hours, preferably about 6 to 18 hours. A reaction temperature is not particularly limited, and the reaction is performed at room temperature to approximately 150° C., preferably 50 to 150° C., and more preferably approximately 80 to 130° C. These conditions can be changed as appropriate depending on the kinds and amounts of the raw materials and the like to be used.

The zinc cluster represented by the general formula (1) is useful for the various catalytic reactions as described above, and is also useful for another application as a raw material for formation of a zinc oxide film. For example, Applied Surface Science (2007), 253(9), 4356-4360 reports that a zinc oxide (ZnO) film which is more uniform than those obtained by conventional production methods is formed when a zinc cluster is formed from a zinc acetate hydrate, which is a raw material, in situ by vacuum heating, then a zinc cluster film is formed on a surface of a substrate, and further the zinc cluster film is subjected to a heat treatment at 500° C. or above.

Meanwhile, Japanese Patent Application Publication No. 2005-305233 discloses that a uniform zinc oxide film can be formed while a zinc cluster is formed in situ by Mist CVD by use of a zinc acetate hydrate. The zinc cluster of the present invention can also be used as a raw material for these processes.

As described above, the zinc cluster of the present invention is useful as a precursor for formation of zinc oxide films and the like.

Hereinafter, the present invention will be described more specifically with reference to Examples, but the present invention is not limited to these Examples at all.

EXAMPLES

In Examples, measurement of products and molecular orbital calculation were carried out under the following conditions and by the following methods.
Conditions for Mass spectrometry (MS):
Apparatus LCMS-IT-TOF (SHIMADZU)
Measuring mode ESI-NEGATIVE MODE
    Interface voltage −3.5 kV
    Nebulizer gas flow rate 1.5 L/min
Solvent DMF
Internal mass calibration TFA-Na (m/z 928.8339, 1064.8087, 1200.7835)
Conditions for Fourier transform infrared spectroscopy:
Apparatus Avatar 360 (manufactured by Nicolet)
Molecular orbital calculation:
Program Gaussian 03 (Gaussian, Inc.)

Example 1

Production of Zinc Cluster

Into a glass tube with one closed end, 30.3 g of zinc trifluoroacetate hydrate (manufactured by Alfa Aesar) (containing 6.6 wt % of water) was introduced. The pressure was reduced to a degree of vacuum of 4×10$^{-1}$ torr with a rotary pump, with a trap cooled in nitrogen being connected to the other end of the glass tube. Subsequently, the glass tube was heated at 120° C. for 1.5 hours with a heater, and then the temperature was gradually raised to 160° C. The glass tube was heated at the same temperature for 30 minutes. The zinc trifluoroacetate hydrate in the glass tube disappeared in approximately 6 hours, and a small amount of a residue was left.

Figure 1:
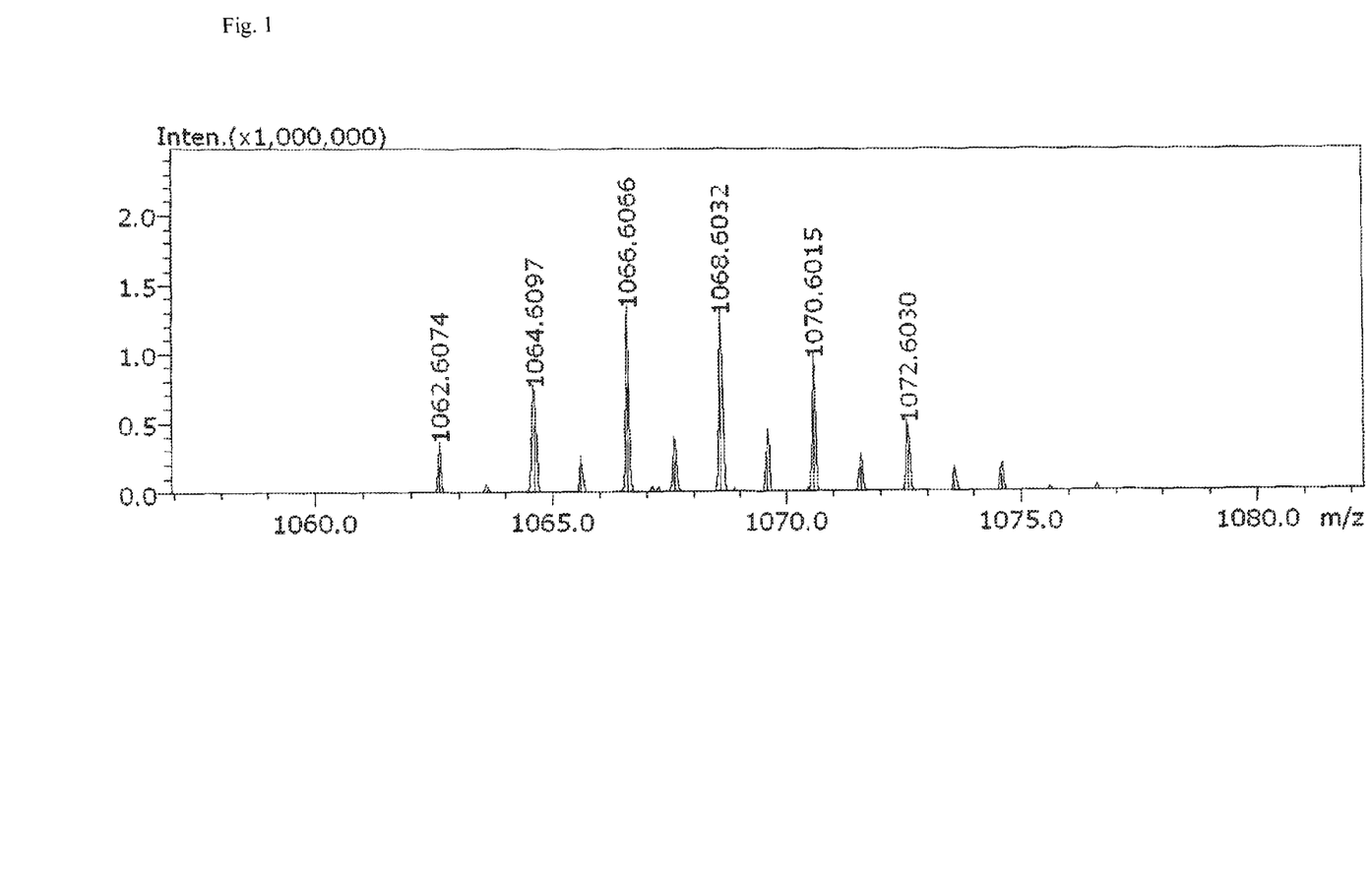
FIG. 1 shows an ESI-MS spectrum of a zinc cluster obtained in Example 1.
Figure 2:
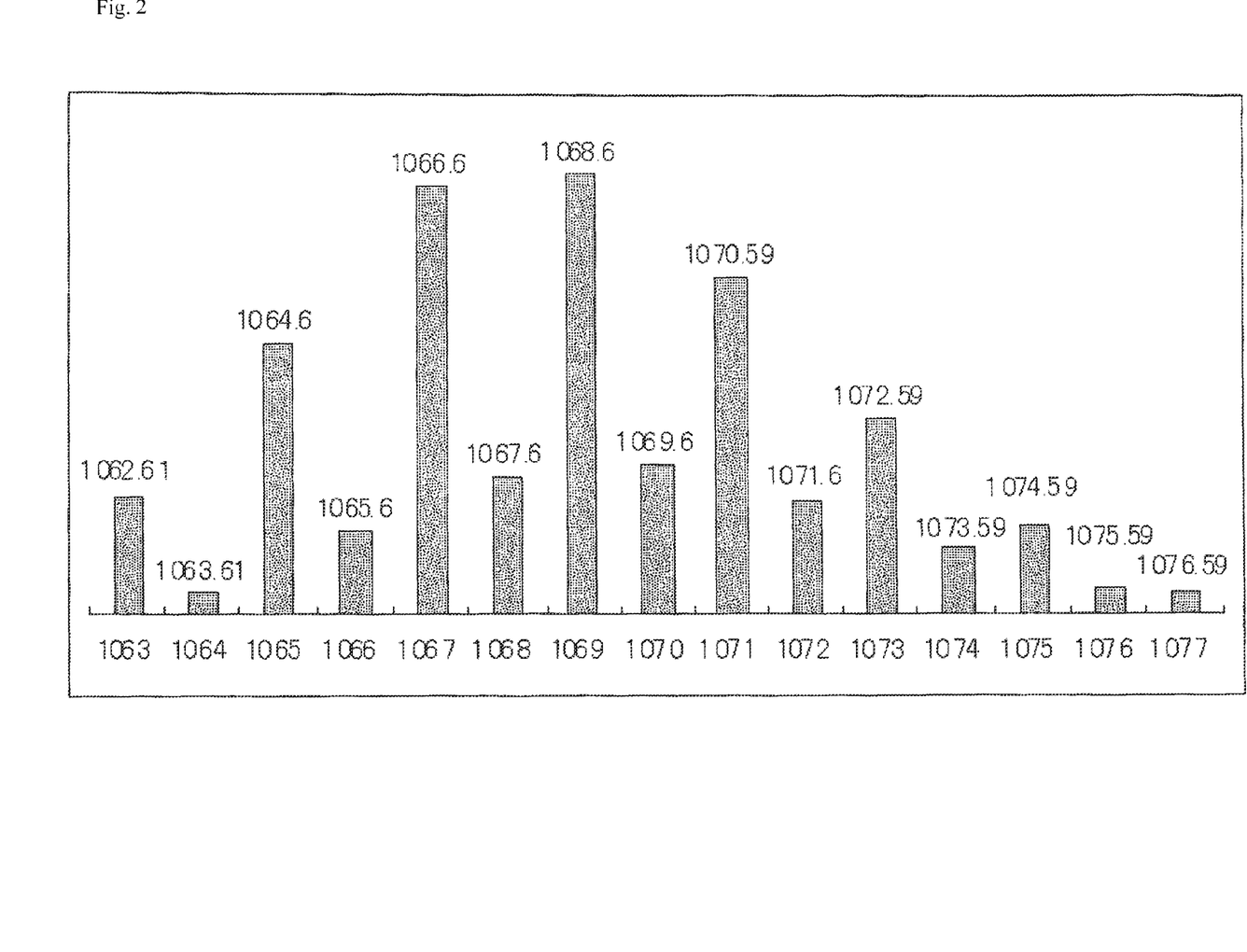
FIG. 2 shows a simulation pattern of an ESI-MS spectrum of $Zn_4O\ (OCOCF_3)_6\ (CF_3COOH)$.

Subsequently, the heating was stopped, and the glass tube was naturally cooled to room temperature. After the cooling, valve provided between the glass tube and the vacuum pump was closed for preventing air and water from entering the glass tube, and, in a glove bag kept under a nitrogen atmosphere, a white solid attached to the glass tube was scraped and collected. The obtained white solid was placed in a Schlenk tube under nitrogen atmosphere, and hermetically closed in a watertight state. Then, the Schlenk tube was taken out from the bag, and the weight of the white solid was measured. As a result, 24.7 g of a zinc cluster was obtained.
Result of Measurement of High-Resolution ES-MS (Negative) Spectrum
Negative ion HR-ESI-MS m/z: 1062.6074
[M−H]$^-$(calcd. For $C_{14}F_{21}O_{15}Zn_4$, 1062.6073); Δ0.09 ppm FIG. 1 shows an ESI-MS spectrum of the zinc cluster produced in Example 1, and FIG. 2 shows a simulation pattern of an ESI-MS spectrum of an anion [$Zn_4O$ ($OCOCF_3)_6$ ($CF_3COO$)]$^{(-)}$ assumable from $Zn_4O$ ($OCOCF_3)_6$ ($CF_3COOH$). The ESI-MS spectrum (FIG. 1) and the simulation pattern (FIG. 2) show similar patterns. In addition, the obtained experimental value 1062.6074 and the value 1062.6073 estimated for the anion [$Zn_4O$ ($OCOCF_3)_6$ ($CF_3COO$)]$^{(-)}$: $C_{14}F_{21}O_{15}Zn_4$ were extremely close to each other with 0.09 ppm. There results indicates the presence of $Zn_4O$ ($OCOCF_3)_6$($CF_3COOH$) in the zinc cluster of the present invention.

In addition, the content of zinc was measured in the following method. Specifically, the zinc cluster obtained in Example 1 (0.0794 g) was weighed into a 200-ml Erlenmeyer flask, and dissolved by adding 50 ml of distilled water thereto. To this mixture, 5 ml of an acetic acid-sodium acetate (pH 5) buffer solution (manufactured by NACALAI TESQUE, INC.) was added, and then the pH was adjusted to approximately 5.5 by adding hexamine little by little. To the neutralized sample solution, several drops of a xylenol orange indicator (Wako Pure Chemical Industries, Ltd., a 0.1 w/v % xylenol orange solution for titration use, 0.1 g/100 ml =0.001396 M) was added. Finally, the volume was adjusted to 100 ml with distilled water. The liquid preparation was titrated with a 0.01 mol/l EDTA standard solution (manufactured by DOJINDO LABORATORIES). The content of zinc was determined (25.20 wt %, theoretical value: 24.48 wt %) from the titer 30.6 ml, at which the color turned from reddish violet to yellow, indicating the endpoint. This result shows $Zn_4O(OCOCF_3)_6(CF_3COOH)_n$ (n=0.72), i.e., a mixture of a zinc cluster $Zn_4O$ ($OCOCF_3)_6$($CF_3COOH$) as a main component with a conventionally known zinc cluster $Zn_4O$ ($OCOCF_3)_6$.

Figure 3:
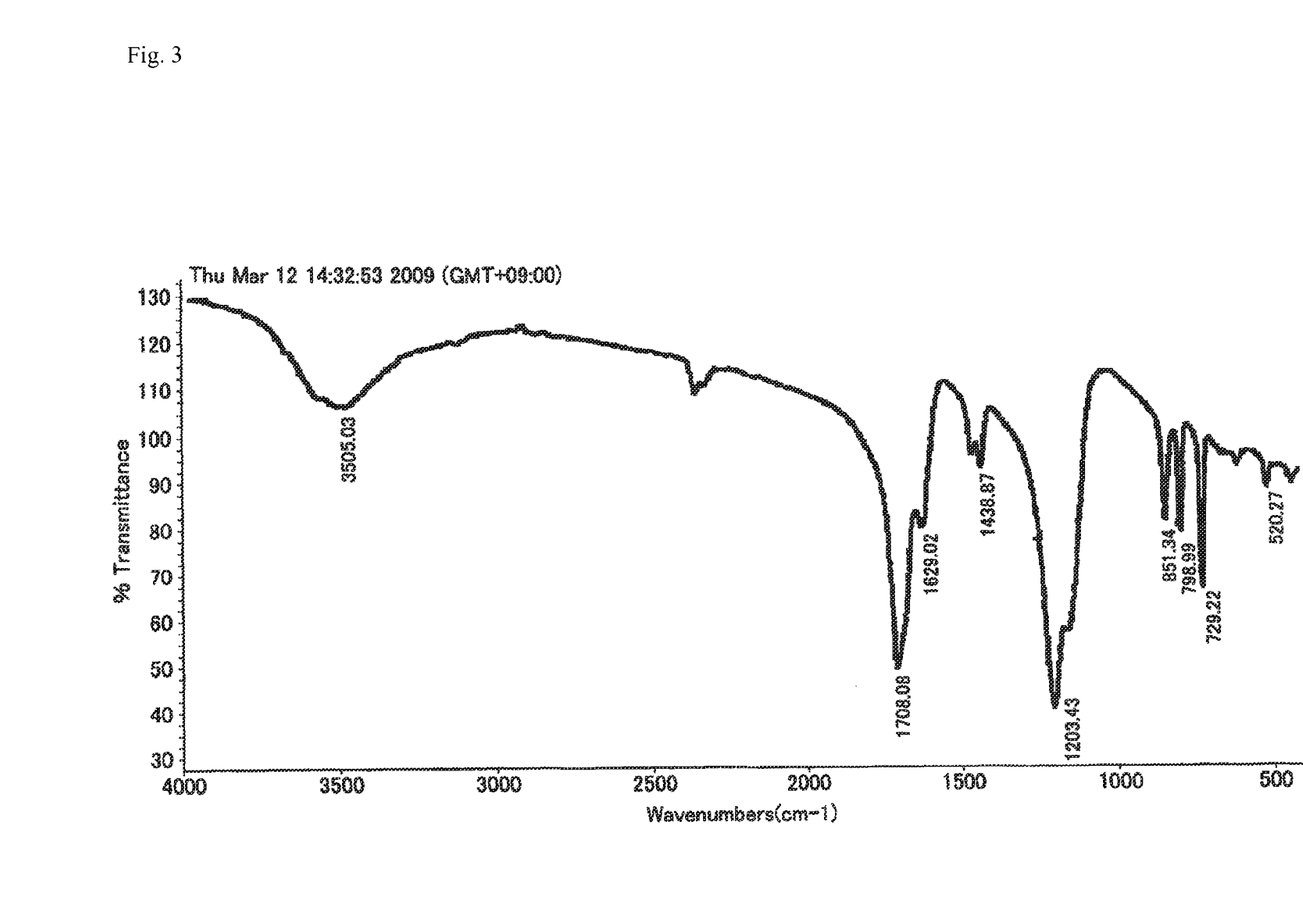
FIG. 3 shows a result of infrared (IR) spectrophotometry of the zinc cluster obtained in Example 1.

In addition, FIG. 3 shows a result of infrared (IR) spectrophotometry of the zinc cluster obtained in Example 1.

Peaks in the IR spectrum were as follows: 426.67 cm$^{-1}$, 520 cm$^{-1}$, 729.22 cm$^{-1}$, 798.99 cm$^{-1}$, 851.34 cm$^{-1}$, 1203.43 cm$^{-1}$, 1438.87 cm$^{-1}$, 1629.02 cm$^{-1}$, and 1708.08 cm$^{-1}$.

Example 2

Esterification Reaction

Under a nitrogen atmosphere, a mixture of 3-phenylpropionic acid (3.0 mmol), n-butanol (3.6 mmol), the zinc cluster obtained in the above-described Example 1 (0.0375 mmol), and diisopropyl ether (5.0 ml) was refluxed for 18 hours. As a result, butyl 3-phenylpropionate was obtained quantitatively.

Example 3

Transesterification Reaction

Under a nitrogen atmosphere, a mixture of methyl 3-phenylpropionate (3.0 mmol), n-butanol (3.6 mmol), the zinc cluster obtained in the above-described Example 1 (0.0375 mmol), and diisopropyl ether (5.0 ml) was refluxed for 18 hours. As a result, butyl 3-phenylpropionate was obtained quantitatively.

Example 4

Transesterification Reaction in the Presence of Alcohol and Amine

Under a nitrogen atmosphere, a mixture of methyl 3-phenylpropionate (3.0 mmol), cyclohexanol (3.6 mmol), cyclohexylamine (3.6 mmol), the zinc cluster obtained in the above-described Example 1 (0.0375 mmol), and diisopropyl ether (5.0 ml) was refluxed for 18 hours. As a result, an ester product, cyclohexyl 3-phenylpropionate, was obtained quantitatively. No formation of an amide product was observed.

Example 5

Production of Zinc Cluster

Into a four-necked flask, 9.70 g of zinc trifluoroacetate hydrate (with a zinc content of 18 wt %, and a water content of 19 wt %) and toluene were introduced. The inside of the flask was replaced with nitrogen, and then the inside pressure of the flask was reduced to 290±10 mmHg with a vacuum pump. Subsequently, the flask was gradually heated. At 60° C., the mixture in the flask become transparent and was completely dissolved. After the temperature reached 75° C., the solvent was recovered at the same temperature. The removed solvent material contained toluene and water. When the amount of water in the recovered solvent reached approximately 20 wt % relative to the amount of the zinc trifluoroacetate hydrate introduced, the heating was stopped. The temperature was gradually lowered to −5° C. After stirring at the same temperature for 4 hours, filtration was performed under nitrogen. The obtained white solid was dried at 75° C./5 mmHg. After the drying, 6.37 g of a white solid was obtained.

The content of zinc in the above-described white solid was determined by the following titration method. Specifically, approximately 30 mg of the white solid obtained as described above was weighed into a 200-ml Erlenmeyer flask, and was dissolved by adding 100 ml of purified water thereto. Further, 5 ml of a buffer solution (acetic acid-sodium acetate, pH 5) was added thereto. Moreover, the pH was adjusted to approximately 5 by gradually adding hexamine (hexamethylenetetramine). Several drops of a xylenol orange indicator solution were added thereto, and the content of zinc was determined by titration with a 0.01 mol/L EDTA standard solution. At the endpoint, the color was changed from reddish violet to yellow. As a result, the content of zinc was 25.58 wt %. This result shows $Zn_4O(OCOCF_3)_6(CF_3COOH)_n$ (n=0.59).

The yield calculated as a zinc cluster trifluoroacetic acid adduct was 89.2%. In addition, the yield in terms of zinc determined from the result of the content of zinc was 93.32%.

Example 6

Transesterification Reaction in the Presence of Amino Group

Under a nitrogen atmosphere, a mixture of 0.6907 g (6 mmol) of 4-piperidine methanol, 64.2 mg (0.06 mmol) of the zinc cluster obtained in the above-described Example 5, and ethyl acetate (10.0 ml) was refluxed for 4 hours. As a result, an ester product was obtained in 85.4%. Formation of 0.7% of an amide product was observed. In addition, a product of concurrent esterification and amidation was obtained in 4.7%. The conversion was 90.9%.

Example 7

Transesterification Reaction

Under a nitrogen atmosphere, a mixture of methyl 3-phenylpropionate (3.0 mmol), t-butanol (3.6 mmol), the zinc cluster obtained in the above-described Example 5 (0.0375 mmol), and diisopropyl ether (5.0 ml) was refluxed for 18 hours. As a result, t-butyl 3-phenylpropionate was obtained quantitatively.

Example 8

Transesterification Reaction

Under a nitrogen atmosphere, a mixture of carbobenzyloxyglycine methyl ester (3.0 mmol), t-butanol (3.6 mmol), the zinc cluster obtained in the above-described Example 5 (0.0375 mmol), and diisopropyl ether (5.0 ml) was refluxed for 18 hours. As a result, carbobenzyloxyglycine t-butyl ester was obtained in a yield of 91.8%.

Example 9

Transesterification Reaction

Under a nitrogen atmosphere, a mixture of (4-((tetrahydro-2H-pyran-2-yloxy)methyl)phenyl)methanol (3.0 mmol), t-butanol (3.6 mmol), the zinc cluster obtained in the above-described Example 5 (0.0375 mmol), and diisopropyl ether (5.0 ml) was refluxed for 18 hours. As a result, 4-((tetrahydro-2H-pyran-2-yloxy)methyl)benzyl acetate was obtained in a yield of 92.9%.

Comparative Example 1

Transesterification Reaction

Under a nitrogen atmosphere, a mixture of methyl 3-phenylpropionate (3.0 mmol), t-butanol (3.6 mmol), a zinc cluster $Zn_4O$ $(OCOF_3)_6$ (0.0375 mmol), and diisopropyl ether (5.0 ml) was refluxed for 18 hours. As a result, t-butyl 3-phenylpropionate was obtained quantitatively.

Comparative Example 2

Transesterification Reaction

Under a nitrogen atmosphere, a mixture of carbobenzyloxyglycine methyl ester (3.0 mmol), t-butanol (3.6 mmol), a zinc cluster $Zn_4O$ $(OCOCF_3)_6$ (0.0375 mmol), and diisopropyl ether (5.0 ml) was refluxed for 18 hours. As a result, carbobenzyloxyglycine t-butyl ester was obtained in a yield of 83.8%.

Comparative Example 3

Transesterification Reaction

Under a nitrogen atmosphere, a mixture of methyl 4-(tetrahydro-2H-pyran-2-yloxy)butyrate (3.0 mmol), t-butanol (3.6 mmol), a zinc cluster $Zn_4O$ $(OCOCF_3)_6$ (0.0375 mmol) and diisopropyl ether (5.0 ml) was refluxed for 18 hours. As a result, t-butyl 4-(tetrahydro-2H-pyran-2-yloxy)butyrate was obtained in a yield of 92.9%.

From these results, the zinc cluster of the present invention exhibited catalytic activities which were equivalent or superior to those of the conventional zinc cluster $Zn_4O$ $(OCOCF_3)_6$.

Example 10

Acetylation Reaction

Under a nitrogen atmosphere, a mixture of ((4-triethylsilyloxy)methyl)phenyl)methanol (6 mmol), the zinc cluster obtained in the above-described Example 5 (0.075 mmol), and ethyl acetate (1.7 ml) was refluxed for 18 hours. As a result, 4-((triethylsilyloxy)methyl)benzyl acetate was obtained in a yield of 86%.

Comparative Example 4

Acetylation Reaction

Under a nitrogen atmosphere, a mixture of (4-((tetrahydro-2H-pyran-2-yloxy)methyl)phenyl)methanol (6 mmol), a zinc cluster $Zn_4O$ $(OCOCF_3)_6$ (0.075 mmol), and ethyl acetate (1.7 ml) was refluxed for 18 hours. As a result, 4-((tetrahydro-2H-pyran-2-yloxy)methyl)benzyl acetate was obtained in a yield of 84%.

From these results, the zinc cluster of the present invention exhibited a catalytic activity which was equivalent or superior to that of the conventional zinc cluster $Zn_4O$ $(OCOCF_3)_6$.

Example 11

Production of Oxazoline

Under a nitrogen atmosphere, a mixture of methyl benzoate (1.5 mmol), (S)-valinol (1.8 mmol), the zinc cluster obtained in the above-described Example 5 (0.0375 mmol), and chlorobenzene (2.5 ml) was refluxed for 12 hours. As a result, (S)-4-isopropyl-2-phenyloxazoline was obtained in a yield of 86%.

Comparative Example 5

Production of Oxazoline

Under a nitrogen atmosphere, a mixture of methyl benzoate (1.5 mmol), (S)-valinol (1.8 mmol), a zinc cluster $Zn_4O$ $(OCOCF_3)_6$ (0.0375 mmol), and chlorobenzene (2.5 ml) was refluxed for 12 hours. As a result, (S)-4-isopropyl-2-phenyloxazoline was obtained in a yield of 84%.

From these results, the zinc cluster of the present invention exhibited a catalytic activity which was equivalent or superior to that of the conventional zinc cluster $Zn_4O$ $(OCOCF_3)_6$.

(Reference Data)

Figure 4:
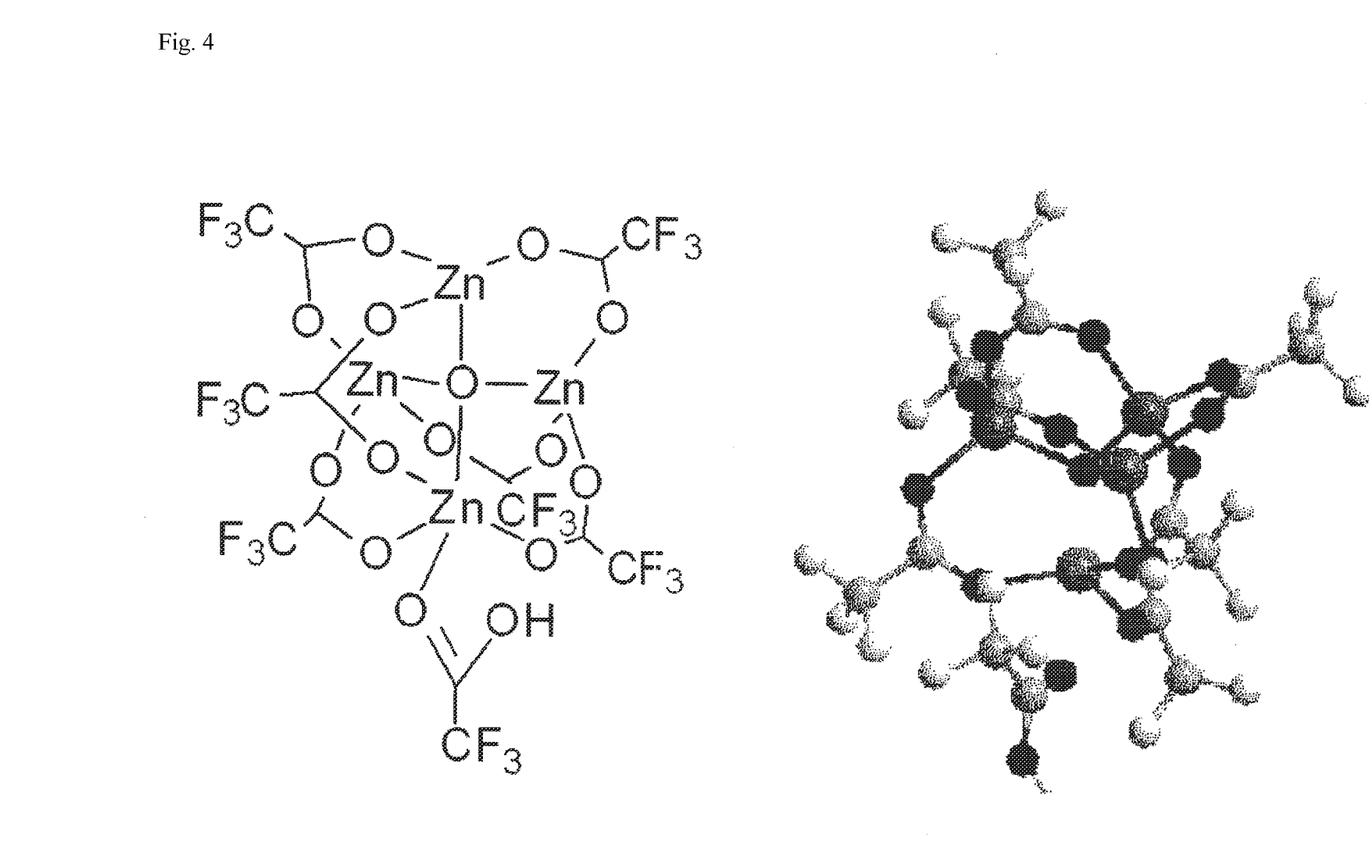
FIG. 4 shows a structure of $[Zn_4O\ (OCOCF_3)_6\ (CF_3COOH)]$, which was estimated from ESI-MS measurement, determined by molecular orbital calculation.

Determination of a structure was attempted for the structure $[Zn_4O\ (OCOCF_3)_6(CF_3COOH)]$ estimated from the ESI-MS measurement by conducting molecular modeling based on molecular orbital calculation. FIG. 4 shows the result. Note that, for the molecular modeling based on molecular orbital calculation, a calculation ((B3LYP/6-31G (d,p))) was conducted by use of Gaussian 03 (Gaussian, Inc.).

Figure 5:
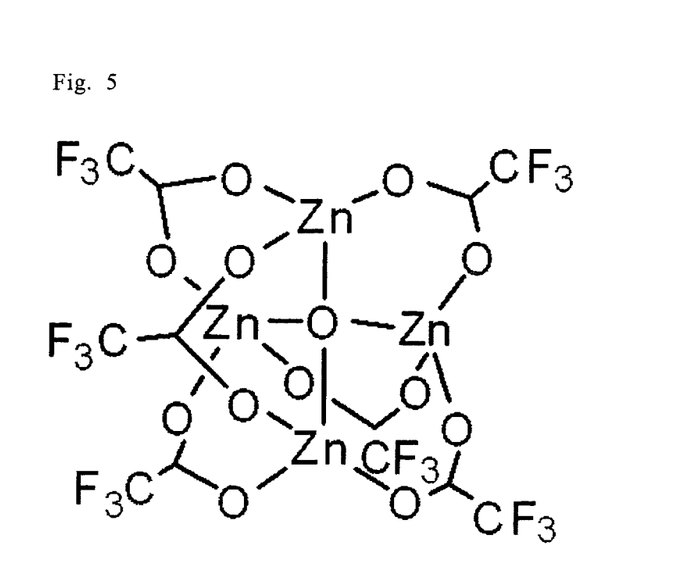
FIG. 5 shows a structure of a zinc tetranuclear cluster $Zn_4O\ (OCOCF_3)_6$ determined by molecular orbital calculation.

An energetically stable structure (FIG. 4) was determined by the molecular orbital calculation. It was revealed that $Zn_4O\ (OCOCF_3)_6(CF_3COOH)$ (FIG. 4) was more energetically stable than the conventionally known zinc tetranuclear cluster $Zn_4O\ (OCOCF_3)_6$ (FIG. 5) by 5.18 Kcal/mol.

The invention claimed is:

1. A zinc cluster represented by general formula (1):

$$Zn_4O\ (OCOR)_6\ (RCOOH)_n \qquad (1),$$

wherein R represents an alkyl group having 1 to 4 carbon atoms which is optionally substituted by one or more halogen atoms, and n represents 0.1 to 1.

2. A method for producing the zinc cluster according to claim 1, comprising performing a reaction by heating a zinc carboxylate hydrate represented by general formula (2):

$$Zn\ (OCOR)_2 \cdot xH_2O \qquad (2),$$

wherein R represents an alkyl group having 1 to 4 carbon atoms which is optionally substituted by one or more halogen atoms, and x represents a number from 1 to 3 at a temperature of 50° C. to 200° C.

3. A method for acylating a hydroxyl group by reacting an alcohol with a carboxylic acid or an ester thereof, and using the zinc cluster according to claim 1 as a catalyst.

4. A method for producing an oxazoline by reacting a carboxylic acid or an ester thereof with an amino alcohol, and using the zinc cluster according to claim 1 as a catalyst.

* * * * *